US00PP10487P

United States Patent [19]

Martins

[11] Patent Number: Plant 10,487

[45] Date of Patent: Jul. 7, 1998

[54] CACTACEAE PLANT NAMED RUDOLPH II

[75] Inventor: Mario Luciano Martins, Half Moon Bay, Calif.

[73] Assignee: Bay City Flower Company, Inc., Half Moon Bay, Calif.

[21] Appl. No.: 814,620

[22] Filed: Mar. 10, 1997

[51] Int. Cl.[6] ..... A01H 5/00

[52] U.S. Cl. ..... Plt./88.5

[58] Field of Search ..... Plt./88.5

*Primary Examiner*—James R. Feyrer
*Attorney, Agent, or Firm*—James R. Cypher

[57] ABSTRACT

The present invention relates to a new and distinct plant variety of the Cactaceae family discovered as a sport in a bench of *Schlumbergera truncata* 'Dark Maria'. The present invention is distinguished from 'Dark Maria' and other known related varieties by a growth habit which combines a "reddish" colored bloom, a strong resistance to bud abscission, a strong propensity for buds to mature and flower, and considerable resistance to fungal diseases. The new variety also possesses the commercially desirable characteristics of a fast growth rate, a strong propensity to branch with minimal pruning, erect stems, and a considerable resistance to nutrient deficiencies.

1 Drawing Sheet

BACKGROUND OF THE INVENTION

The present invention relates to a new and distinct variety of the Cactaceae family. The new variety is named *Schlumbergera truncata* "Rudolph II" by the inventor. The inventor is Mario Luciano Martins of Half Moon Bay, Calif., a citizen of the United States.

Many varieties of *Schlumbergera truncata* tend to bloom in the months of November and December in the Northern Hemisphere. Because of their blooming time, there is a large market for these varieties during the Thanksgiving and Christmas seasons as a decorative plant. In fact, one common name for the species is Christmas Cactus.

There are many commercially developed varieties of *Schlumbergera truncata*. Patented varieties include: 'Lavendar Doll' (Cobia, U.S. Plant Pat. No. 3,690); 'Christmas Charm' (Cobia et al., U.S. Plant Pat. No. 4,196); 'Rudolph' (Higaki, U.S. Plant Pat. No. 6,234); and 'Dasher' (Higaki, U.S. Plant Pat. No. 7,367).

For many varieties of the species, bud abscission is a problem: a large portion of the initial buds that form on the plant fall off before they mature. Furthermore, many cultivars possess the further undesirable characteristic that no more than 50% of the buds set on the plant actually fully mature and bloom. Preferred cultivars resist bud abscission, as well as produce buds that have a propensity to mature.

Commercially preferred varieties also possess: a fast growth habit, an upright and dense appearance, and a resistance to fungal diseases and nutrient deficiencies. In addition, certain colors, such as those within the red group are often preferred as red is a common color for decorating during the Christmas season.

The new variety is reddish in color and possesses all the above mentioned characteristics.

This new variety of *Schlumbergera truncata* was discovered by the inventor as a sport in a cultivated bench of *Schlumbergera truncata* 'Dark Maria' at a nursery in the city of the Half Moon Bay. Half Moon Bay is located in the county of San Mateo, in the state of California.

The inventor first identified the sport as a new variety by how its flowers differed in color and morphology from the variety 'Dark Maria'. The blade margins of the tepals of 'Dark Maria' are R.H.S. 46A (red group). The middle portion of the tepal blades is R.H.S. 42C (red group). The base of the tepal blades are R.H.S. 155A (white group). The contrasting color of the blades gives 'Dark Maria' a two-toned appearance. 'Dark Maria' is also characterized by highly reflexed tepals. In comparison, most of the exposed blades of the tepals of the new variety are almost uniformly R.H.S. 47A (red group). The more hidden tube portions of some of the tepals, like 'Dark Maria', are R.H.S. 155A (white group). The new variety is distinguished from 'Dark Maria' by its tepals which are more uniformly colored and which are not as reflexed as 'Dark Maria'.

Further comparisons to 'Dark Mark' and other commercially produced varieties showed the new variety to have an improved resistance to bud abscission and that the buds that remained on the plant showed a improved propensity to mature and flower. During asexual reproduction and development, the new variety was also found to have better resistance to fungal diseases than certain commercially produced varieties.

The characteristics of this new variety which in combination distinguish it from *Schlumbergera truncata* 'Dark Maria' and all other varieties known to the inventor are:

1. the color of its flower;

2. an improved resistance to bud abscission over the varieties, 'Dark Maria', 'Rudolph', 'Dasher', 'White Christmas', 'Christmas Fantasy', and 'Camellia';

3. a greater propensity for buds to mature and flower over the varieties 'Dark Maria', 'Rudolph', 'Dasher', 'White Christmas', 'Christmas Fantasy', and 'Camellia'; and 4. an improved resistance to fungal diseases over the varieties, 'Dark Maria', 'Rudolph', 'Dasher', 'White Christmas', 'Christmas Fantasy', and, 'Camellia'.

The overall reddish appearance of the flower is due to the generally even-toned color of its tepals. The dominant color of the blades of the sepaloid tepals, the tube laminating tepals, and the tube forming tepals is R.H.S. 47A (red group).

The new variety's improved resistance to bud abscission results in the setting of 1 to 2 buds per phylloclade.

Because the buds of the new variety have a greater propensity to mature, 50 to 80 percent of the buds that do set mature and bloom.

The distinguishing characteristics of the new variety are retained by asexually reproduced, successive generations.

In addition, the new variety also possesses the additional commercially desirable characteristics of:

1. a fast growth rate;

2. a strong propensity to branch with minimal pruning, resulting in a dense appearance;

3. erect stems, resulting in an upright appearance; and 4. a considerable resistance to nutrient deficiencies.

The new variety can grow 16.5 cm high in 15 cm pots in 12 to 14 months, depending on whether it was propagated in the winter or the summer. Cuttings propagated in the summer grow more quickly.

The new variety generally forms two branches from the propagated cutting, and three more after a single pruning.

The inventor has asexually reproduced the new variety at a commercial nursery in Half Moon Bay, Calif. through three successive generations by cuttings, and has found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
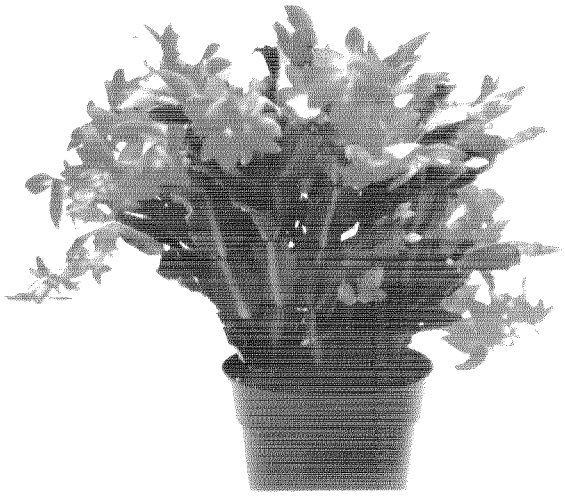
FIG. 1 is a color photograph of a potted plant of the new variety illustrating the overall appearance and form of the plant, and the abundance of blooms.
Figure 2:
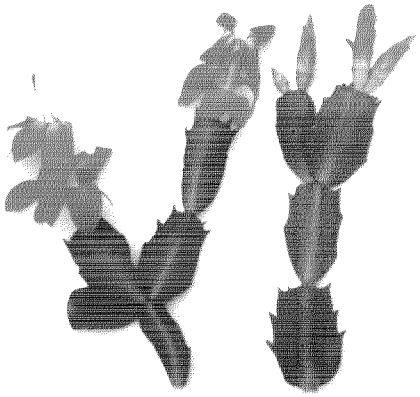
FIG. 2 is a color photograph of two individual branches of the new variety.
Figure 3:
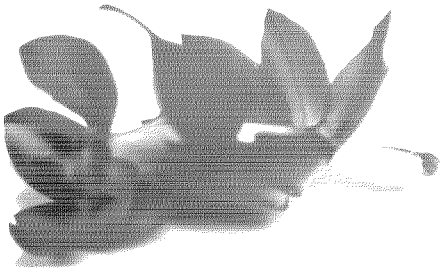
FIG. 3 is a color photograph showing a side view of a fully opened bloom of the new variety.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to the R.H.S. Colour Chart published by The Royal Horticultural Society of London, England.

The plants observed were grown in 15 cm pots. The plants were 12 months old and approximately 16.5 cm high. The following description is based on observations of optimally fertilized plants grown under 50–70% shaded polyhouse nursery conditions in Half Moon Bay, Calif. Temperatures in Half Moon Bay on average range from 55 to 65 degrees Fahrenheit in the summer months, and from 45 to 55 degrees Fahrenheit in the winter months.

DETAILED PLANT DESCRIPTION

Name: *Schlumbergera truncata* 'Rudolph II'.

Parentage: Unknown. Found as a variant or sport in a bench of 'Dark Maria.' Most closely resembles the known variety 'Dark Maria.'

Classification:

*Family.*—Cactaceae.

*Tribe.*—Cereus (Cacteae).

*Genus.*—Sclumbergera.

*Species.*—*Schlumbergera truncata* (Haw.) Moran [*Epiphyllum truncatum* Haw.; *Zygocactus truncatus* (Haw.) K. Schum.]. Bailey and Bailey and the staff of the Bailey Hortorium, *Hortus Third* (1976).

*Commercial.*—Thanksgiving Cactus, Christmas Cactus.

Form: Terrestrial, shade-loving, succulent, leafless plant with jointed and branched stems.

Stems:

*General.*—Irregular with usually mono-chotomous to di-chotomous branching of upright, adventitiously rootable, flattened phylloclades that have a prominent midrib and prominently toothed lateral wings.

*Phylloclades.*—General: Elongated and flat with transversely elongated, areole bearing, truncated apex, with inwardly tapering basal wing margins that merge through a broad, usually pointed, basal juncture with the phylloclade therebelow, and with an axiallary areole associated with each tooth.

*Midrib.*—General—Extends longitudinally of phylloclade and continuously through joints with laterally tapering cortex at wing insertions. Pith surrounds the vascular bundles that branch and provide lateral extensions of the vascular system to marginal teeth. Texture—Smooth, waxy epidermis with wax in small embedded scales and becoming corky in basal stem areas with age. Size—Length: Usually between 55 mm and 65 mm. Thickness: 3 to 4 mm at the center, and tapering to 1 mm at the edges. Color—Mature plants: R.H.S. 147A (yellow-green group) Immature plants: R.H.S. 147B to 152B (yellow-green group).

*Wings.*—General shape—Generally flattened from midrib cortex to tooth insertions with slight thinning taper toward margins. Margins—Toothed (modified leaves). Texture—Succulent to leathery with smooth, waxy epidermis having wax arranged in small embedded scales and becoming corky in basal plant areas with age. Size—Center thickness: 3–4 mm. Width: Usually 40 mm, up to 50 mm. Color (at maturity)—R.H.S. 147B (yellow-green group).

*Teeth.*—General shape—Generally flattened and tapering along margins from wing insertion to an apex having a hyaline, single cell, pointed spine with nonpredictable bending. Adaxial margin shape: Generally straight but with both concave and convex adaxial margin tendencies. Abaxial margin shape: Irregular with tendencies toward a medial indentation that provides a distal terminus for a convex proximal marginal edge portion and a basal terminus for a distal marginal edge portion that varies from straight to convex. Orientation—Usually projects generally distally of the phylloclade base in an alternate arrangement. Margins—Entire. Texture—Succulent to leathery with a smooth waxy epidermis having wax in small embedded scales and becoming corky in basal plant areas with age. Number—Usually 3 to 4 on each side. Size—Center thickness: 1 mm. Areole to apex dimension (adaxial margin side): usually 7 to 8 mm in length, up to 11 mm.

*Areoles.*—Terminal areole—Large, elongated, oval-shaped with several acicular bristles, copious multicellular hairs, and several buds that may mature into either new phylloclades or flowers. The opposite ends of the areole are located adjacent to subsidiary areoles which are in turn located at the axils of teeth that are located at the distal end of phylloclade. Axiallary areaoles—Acicular bristles without glochidia but having copious, short, brownish to colorless, multi-cellular hairs. Areoles are commonly found in the basal portion of the phylloclade in association with a vestigial tooth that is less than 1 mm in length. (Vestigial teeth not considered in teeth number or length of teeth.)

Buds: Unarmored, ovid and chlorophyllous.

Flowers:

*Bloom life.*—8 to 9 Days.

*General.*—Sessile, zygomorphic, usually solitary, terminal, perfect, and epigynous with double hypanthium and tepals (undifferentiated whorled sepals and petals) having a spiral emergence as a perianth provided with a sepaloid series of free tepals, a tube laminating series of tepals, and a tube forming series of united tepals.

*Sepaloid series of tepals.*—General: Free tepals inserted on top of the ovary. Shape: Deltoid in outer members of the whorl and grading inwardly on the whorl to tepals which are usually either obovate or ovate and less frequently elliptical. Tips are broadly acuminate with some acute tendencies, and margins are entire with sparse irregular teeth appearing mainly in the apex areas. Texture: Succulent and glabrous outer whorl members and grading inwardly in the whorl to silken blades with fleshly basal areas. Number: Usually 8. Size (at full bloom): Base-tip dimension—9 mm to 17 mm maximum. Width dimension—7 mm to 10 mm maximum. Color: R.H.S. 47A (red group).

*Tube laminating series of tepals.*—General: Tepals inserted on ovary and basally united below the throat as outer laminations on the perianth tube and with progressively greater amounts of basal fusion inwardly in the whorl. Number: 8. Size (at full bloom): Shape: Grading inwardly in the whorl with progressively longer base-tip dimensions and with blade areas changing inwardly from obovate to broadly elliptical and with acute tips. Entire margins with sparse irregular teeth mainly in apex areas. Texture: Succulent, slightly fleshly basal areas with silken blades. Number: 6. Size (at full bloom): Base-tip dimension—47 mm to 61 mm maximum. Width dimension—14 and 15 mm maximum. Color: R.H.S. 47A (red group).

*Tube forming series of tepals.*—General: Tepals basally united to form a hollow perianth tube that is inserted on ovary and equipped with a irregular carina (keel) at the throat. Shape: Perianth tube—Elongated and ellipsoidal to oval in cross-section. Blades—Generally elliptic to broadly elliptic with obovate tendencies and with acuminate tips. Entire margins with sparse, irregular teeth mainly in apex area. Carina (keel)—Transcending and irregular. Texture: Perianth tube—Thick, succulent, and slightly ribbed. Blades—Translucent and silken. Carina (keel)—Fleshy. Blade number: 5. Size (at full bloom): Perianth tube—Base to keel length: 37 mm. Blades—Maximum length (keel to tip): 36 mm. Minimum length (keel to tip): 31 mm. Maximum width: 15 mm. Minimum width: 7 mm. Color (at full bloom): Perianth tube—R.H.S. 49D (red group). Blades—R.H.S. 47A (red group). Orientation at full bloom: mildly reflexed to reflexed.

*Androecium* (stamens).—General: Numerous exserted and diadelphous stamens with one group having filaments basally fused to the perianth tube and the other group having filaments basally united to form a nectary housing; thin annulus around the style, which is provided with a thin, deflexed, irregularly toothed margin or ruffle at the throat of the annulus. Stamen number: Tube attached group—94 to 100 individual stamen. Basally united group—17 individual stamen. Filament: General—Translucent and glabrous with anther connective. Shape—Long, slender and gradually tapering from base to anther connective. Texture—Glabrous and silken. Color—Translucent white; individually, R.H.S. 155C (white group); collectively, R.H.S. 155B (white group). Size (at full bloom)—Length: 49 mm to 62 mm. Diameter (width): 0.5 mm. Anthers: Shape—Rod shaped. Size—Length: 1 mm. Width: 0.33 mm. Texture—Course or grainy. Color (pollen color)—R.H.S. 4C (yellow group).

*Gynoecium* (pistil).—General: Compound, parietal placentation with united style surrounded by an annular diffuse nectary at its insertion. Style: General—Stout and inserted in ovary. Shape—Elongated and terrete. Texture—Fleshy and glabrous with short inner glutinous hairs at distal end. Color—R.H.S. 45B (red group). Size (at full bloom)—Length: 59 to 60 mm. Diameter (width): 1 mm. Stigma: General—Exserted and erect with usually 6 or 7 inner marginally adhering lobes. Shape—Elongated and tapering toward lobe tips and having relatively blunt apices. Texture—Fleshy and smooth with short glutinous hairs. Color—R.H.S. 74A (red-purple group). Size—Length: 3 mm. Width (at base): 0.75 mm. Ovary: General—Epigynous with thin epidermis and distally located concavity, and with a single cavity usually having 6 or 7 carpels with numerous ovules. Shape—Terrete to ovoid and generally broadening from insertion to floral end. Texture—Succulent and glabrous with thin outer epidermis. Color—Internally white; externally R.H.S. 146C (yellow-green group). Size (at full bloom)—Length: 4 mm. Width: 3 mm.

I claim:

1. The new and distinct variety of cactus plant substantially as herein shown and described.

* * * * *